(12) United States Patent
Kratz

(10) Patent No.: US 10,220,101 B2
(45) Date of Patent: Mar. 5, 2019

(54) COMBINATION OF DRUGS WITH PROTEIN-BINDING PRODRUGS

(75) Inventor: Felix Kratz, Ehrenkirchen (DE)

(73) Assignee: Vergell Medical S.A., Geneva (CH)

( * ) Notice: Subject to any disclaimer, the term of this patent is extended or adjusted under 35 U.S.C. 154(b) by 0 days.

(21) Appl. No.: 13/641,284

(22) PCT Filed: Apr. 13, 2011

(86) PCT No.: PCT/EP2011/001874
§ 371 (c)(1),
(2), (4) Date: Oct. 30, 2012

(87) PCT Pub. No.: WO2011/131314
PCT Pub. Date: Oct. 27, 2011

(65) Prior Publication Data
US 2013/0040905 A1 Feb. 14, 2013

(30) Foreign Application Priority Data
Apr. 19, 2010 (EP) .................... 10004143

(51) Int. Cl.
| A61K 38/00 | (2006.01) |
| A61P 35/00 | (2006.01) |
| A61K 31/704 | (2006.01) |
| C07H 17/08 | (2006.01) |
| A01N 43/04 | (2006.01) |
| A61K 31/70 | (2006.01) |
| A61K 47/64 | (2017.01) |
| A61K 47/65 | (2017.01) |
| A61K 47/54 | (2017.01) |

(52) U.S. Cl.
CPC ............ *A61K 47/64* (2017.08); *A61K 31/704* (2013.01); *A61K 47/54* (2017.08); *A61K 47/6455* (2017.08); *A61K 47/65* (2017.08); *A61P 35/00* (2018.01); *A61K 2300/00* (2013.01)

(58) Field of Classification Search
None
See application file for complete search history.

(56) References Cited

U.S. PATENT DOCUMENTS

| 7,445,764 | B1 * | 11/2008 | Kratz | 424/1.69 |
| 7,902,144 | B2 * | 3/2011 | Kratz | 514/15.2 |
| 2005/0250835 | A1 * | 11/2005 | Wang | 514/411 |
| 2006/0263434 | A1 * | 11/2006 | Desai | A61K 9/0019 424/489 |
| 2007/0190068 | A1 * | 8/2007 | Hart et al. | 424/179.1 |
| 2010/0111866 | A1 * | 5/2010 | Kratz | 424/9.1 |
| 2010/0144647 | A1 * | 6/2010 | Kratz et al. | 514/18 |
| 2011/0117009 | A1 * | 5/2011 | Kratz et al. | 424/1.11 |
| 2017/0319707 | A1 * | 11/2017 | Kratz | A61K 31/704 |
| 2018/0028679 | A1 * | 2/2018 | Kratz | A61K 31/519 |

FOREIGN PATENT DOCUMENTS

| WO | 92/21356 A1 | 12/1992 | |
| WO | 1999026620 | 6/1999 | |
| WO | WO 9926620 A1 * | 6/1999 | ............ A61K 31/23 |
| WO | 2000/076551 A2 | 12/2000 | |
| WO | 02/41904 A1 | 5/2002 | |
| WO | 2004/011499 A1 | 2/2004 | |
| WO | 2004/071524 A1 | 8/2004 | |
| WO | 2007/005941 A2 | 1/2007 | |
| WO | 2007005941 | 1/2007 | |
| WO | 2008098789 | 8/2008 | |
| WO | WO 2008098789 A2 * | 8/2008 | ............ A61K 47/48 |
| WO | 2008/143916 A2 | 11/2008 | |
| WO | 2009/097397 A2 | 8/2009 | |
| WO | 2009097397 | 8/2009 | |
| WO | WO 2009097397 A2 * | 8/2009 | ........... A61K 39/395 |

OTHER PUBLICATIONS

Das, U., "Albumin and Lipid Enriched Albumin for the Critically Ill," J. Assoc. of Physicians of India 57:53-59 (2009).*
U.S. Appl. No. 12/964,099, filed Dec. 2010, Raucher et al.*
ASHP Guidelines on Clinical Drug Research, available online at http://www.ashp.org/DocLibrary/BestPractices/ResearchGdlClinical.aspx, pp. 486-492 (1998).*
"Composition," available online at http://www.thefreedictionary.com/p/composition, 6 pages (accessed 2014).*
Kratz, Expert Opin. Investig. Drugs 16:855-866 (2007).*
Hortobagyi, Drugs 54.Suppl. 4:1-7 (1997).*
Terrie, "Monitoring Combination Drug Therapy", available online at http://www.pharmacytimes.com/print.php?url=/publications/issue/2010/january2010/rxfocuscombination-0110, 7 pages (Jan. 2010).*
Harries et al., "Phase I/II study of DHA-paclitaxel in combination with carboplatin in patients with advanced malignant solid tumours," British Journal of Cancer, vol. 91, No. 9, Nov. 1, 2004, pp. 1651-1655.
Graeser et al., "INNO-206, the (6-maleimidocaproyl hydrazone derivative of doxorubicin), shows superior antitumor efficacy compared to doxorubicin in different tumor xenograft models and in an orthotopic pancreas carcinoma model," Investigational New Drugs, vol. 28, Jan. 8, 2009, pp. 14-19.
Harries, M., et al., "Phase I/II Study of DHA-Paclitaxel in Combination with Carboplatin in Patients with Advanced Malignant Solid Tumours", British Journal of Cancer, 2004, vol. 91, pp. 1651-1655.
Korean Office Action received from Korean Intellectual Property Office for Korean Patent Application No. 10-2012-7030273, dated Nov. 1, 2016.
English Translation of Korean Office Action received from Korean Intellectual Property Office for Korean Patent Application No. 10-2012-7030273, dated Nov. 1, 2016.

* cited by examiner

*Primary Examiner* — James H Alstrum-Acevedo
*Assistant Examiner* — Thea D'Ambrosio
(74) *Attorney, Agent, or Firm* — McDonnell Boehnen Hulbert & Berghoff LLP

(57) ABSTRACT

The present invention relates to a composition and a combination comprising at least one first drug and at least one protein-binding prodrug, wherein the proteinbinding prodrug comprises a protein-binding group, a second drug, and a linker that can be cleaved hydrolytically, enzymatically, or in a pH-dependent manner in the body, as well as to a kit and a pharmaceutical composition comprising said composition or combination.

5 Claims, 3 Drawing Sheets

Figure 1:
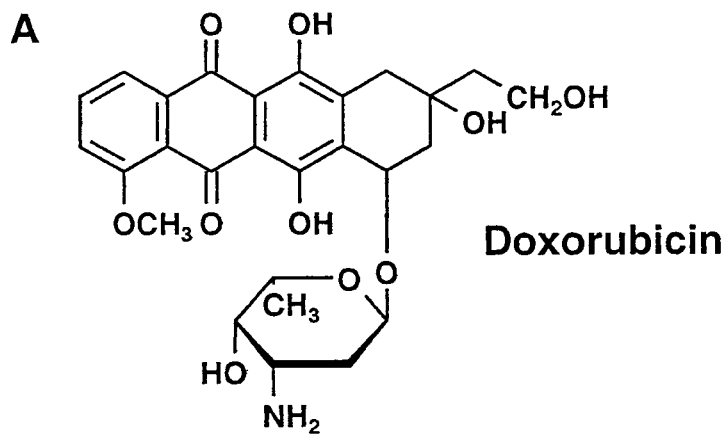
Figure 1:
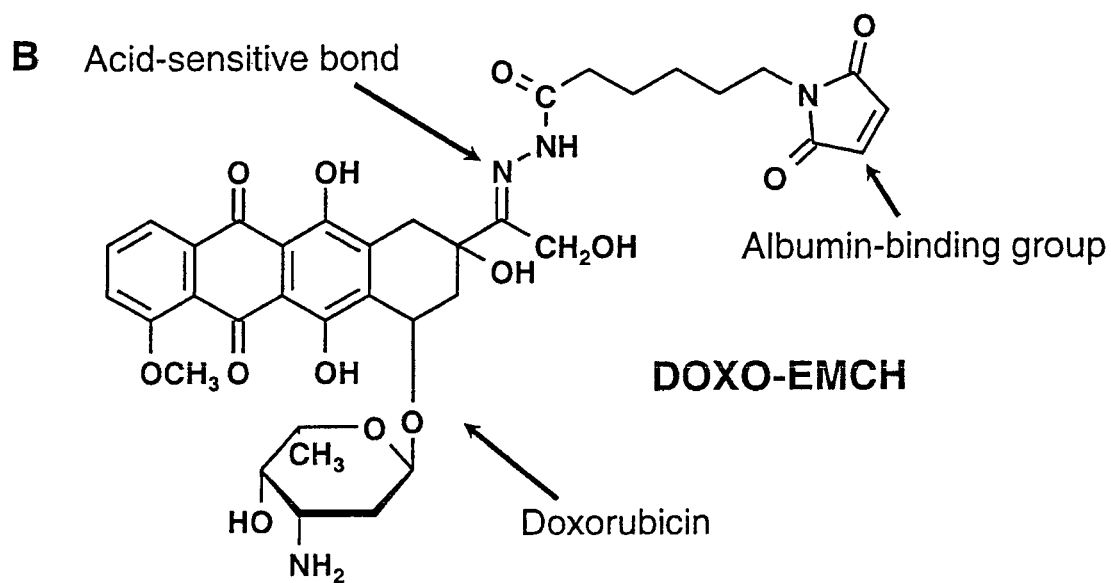

Specification includes a Sequence Listing.

COMBINATION OF DRUGS WITH PROTEIN-BINDING PRODRUGS

CROSS REFERENCE TO RELATED APPLICATIONS

The present application is a 35 U.S.C. 371 National Application of PCT/EP2011/001874, filed Apr. 13, 2011, which claims priority to European Patent Application No. 10004143.3, filed Apr. 19, 2010.

The present invention relates to a composition and a combination comprising at least one first drug and at least one protein-binding prodrug, wherein the protein-binding prodrug comprises a protein-binding group, a second drug, and a linker that can be cleaved hydrolytically, enzymatically, or in a pH-dependent manner in the body, as well as to a kit and a pharmaceutical composition comprising said composition or combination.

Most of the drugs used at present are compounds having low molecular weights and exhibit, when systemically administered to a patient, a high plasma clearance or total body clearance. Furthermore, said low molecular weight compounds show a high tendency to penetrate body tissues by diffusion, resulting in a uniform biodistribution. These are the two main reasons why only small quantities of the drug reach the site of action and, due to distribution over healthy tissues of the body, said drugs give rise to problematic side-effects. These disadvantages are of particular concern for those drugs having a high cytotoxic potential, such as cytotoxic agents, immunosuppressive agents or virostatic agents.

Several strategies have been pursued for improving the selectivity of low molecular weight drugs and thus to increase the concentration of the active agent in the desired tissue, while the concentration of the same is decreased in healthy tissues in order to reduce side-effects.

Carriers, such as for example albumin, or its drug conjugates exhibit a markedly long half-life in the systemic circulation of up to 19 days. Because of an elevated permeability of vessel walls of the e.g. malignant, infected or inflamed tissue for macromolecules, the carrier, such as for example serum albumin, passes preferentially into the target tissue. In this context, prodrugs have been presented which bind in situ to e.g. human serum albumin and show improved properties in contrast to the drug alone. In addition, antibodies, peptides or synthetic polymers have been investigated as drug carriers for the development of prodrugs.

However, although such prodrugs have been shown to allow a more specific delivering of the active agent to the target tissue in most cases, it is desirable to further enhance the efficacy and in vivo tolerability of such agents for an improved treatment.

Therefore, the technical problem underlying the present invention is to provide more efficient and/or more tolerable pharmaceutical compositions that can be used in the treatment of various diseases.

The solution to the above technical problem is achieved by the embodiments characterized in the claims.

In particular, it has been found that combinations of protein-binding prodrugs with low-molecular weight drugs surprisingly produce better therapeutic effects and tolerability in vivo than either the prodrug or the low-molecular weight drug alone.

Therefore, in one aspect the present invention relates to a composition comprising a combination of at least one first drug and at least one protein-binding prodrug, wherein the protein-binding prodrug comprises a protein-binding group, a second drug, and a linker that can be cleaved hydrolytically, enzymatically, or in a pH-dependent manner, and wherein the at least one first drug and the second drug contained in the prodrug are the same or different.

The term "prodrug" as used herein relates to any form of a drug which is administered to an organism, such as a human, in an inactive or less active form and is converted, e.g. by metabolization, into the active form. Said conversion of the prodrug into the active form is not specifically restricted and includes any chemical and/or physical alteration of the prodrug which occurs after administration, such as for example release of an active part of the prodrug at the site of action by hydrolytic, enzymatic and/or pH-dependent cleavage.

According to the present invention, there is no specific restriction as to how the components of the prodrug of the composition of the present invention, i.e. the protein-binding group, the second drug, and the cleavable linker are connected to each other, as long as the second drug is bound to the cleavable linker and the biological function of the protein-binding group and the second drug are not negatively affected by the structural setup. The molecular structure of the prodrug of the composition of the present invention may for example have a linear form or a branched form or is present in a circular form.

According to the present invention, there is no specific restriction concerning the structural setup of the prodrug of the composition of the present invention, i.e. the way the constituents of the above-defined prodrug are chemically bonded together. In particular, the prodrug of the composition according to the present invention may contain one or more spacers in any position between the constituents of the above-defined prodrug, i.e. the protein-binding group may for example be bound to the rest of the prodrug through a spacer or, as another example, the second drug may be bound to the cleavable linker through a spacer. Furthermore, the function of e.g. the cleavable linker may be incorporated in such a spacer, i.e. a spacer may be used between the second drug and the rest of the prodrug which can also serve as the cleavable linker. It is also possible to bind the second drug, the cleavable linker, and/or the protein-binding group to a central group, which may be linear or branched, such as a peptide, a sugar, a heterocyclic group, or any inorganic or organic compound suitable to bind one or more of the constituents of the prodrug.

The term "protein-binding group" as used herein is not specifically restricted and relates to any functional group which is capable of binding to an amino, a hydroxy or thiol group of a compound which may be of endogenous or exogenous origin. Preferred examples of a protein-binding group according to the present invention are a maleinimide group, a halogenacetamide group, a halogenacetate group, a pyridylthio group, a vinylcarbonyl group, an aziridin group, a disulfide group, a substituted or unsubstituted acetylene group, and a hy-droxysuccinimide ester group. In a particularly preferred embodiment of the composition of the present invention, the protein-binding group is a maleinimide group. The protein-binding group also includes functional groups, such as —COOH or —SO$_3$H, that can be activated by standard coupling agents, e.g. dicyclocarbodiimides, acid chlorides, or peptide coupling reagents (e.g., BOP, HATU, PyBOP).

One or several prodrugs can be bound to any suitable carrier such as peptides, sugars, serum proteins, antibodies or antibody fragments, growth factors, polysaccharides, or synthetic polymers. The carrier in general contains suitable functional groups such as hydroxy, amino or thiol groups to bind the protein-binding prodrug. If necessary, these can be introduced in the carrier molecule by chemical modification through techniques known to those skilled in the art.

In a preferred embodiment, the protein-binding group of the prodrug of the composition according to the present invention allows said prodrug to bind in situ after administration by e.g. injection to components of body fluids and/or tissue components, preferably to serum proteins and more preferably to serum albumin, particularly to cysteine-34 of serum albumin and are then present as macromolecular prodrugs which carry the second drug to the target site. In a particularly preferred embodiment of the composition of the present invention, the protein-binding group of the above-defined prodrug binds in situ to cysteine-34 of albumin.

The term "cleavable linker" as used herein relates to any linker which can be cleaved physically or chemically. Examples for physical cleavage may be cleavage by light, radioactive emission or heat, while examples for chemical cleavage include cleavage by redox-reactions, hydrolysis, pH-dependent cleavage or cleavage by enzymes. Cleavage of the cleavable linker according to the present invention can be performed in vivo, e.g. in the body of a patient, e.g. a human patient.

According to a preferred embodiment of the composition of the present invention, the cleavable linker comprises one or more hydrolytically cleavable bonds, the hydrolysis of which releases the second drug. Examples for hydrolytically cleavable bonds are ester bonds or metal-complex bonds, such as are present in platinum-dicarboxylate complexes, where a diaminediaquoplatinum(II) complex is liberated.

In another preferred embodiment of the composition of the present invention, the cleavable linker may be cleavable by an enzyme. For example, the cleavable linker of the composition of the present invention may contain at least one peptide bond which preferably lies within a cleavable peptide sequence of a protease. A peptide bond can therefore be implemented by the insertion of a respective peptide sequence into the cleavable linker. Suitable enzymes are, for example, proteases and peptidases, e.g. matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. Preferred examples of proteases according to the present invention are in particular MMP-2, MMP-3 and MMP-9, cathepsin B, H, L and D, plasmin, urokinase, and prostate-specific antigen (PSA). Preferred peptide sequences that are incorporated in the prodrug are: Arg, Arg-Arg, Phe-Arg, Phe-Cit, Ile-Pro-Lys, Lys-Lys, Arg-Lys, Ala-Leu-Ala-Leu [SEQ ID NO: 1], Phe-Lys, Phe-Lys-Ala, Val-Cit, Val-Arg, Ala-Phe-Lys, D-Ala-Phe-Lys, Met, Met-Met, Phe-Met, Tyr-Met, Ala-Met, Ala-Phe-Met, Phe-Ala-Met, Ala-Tyr-Met, Phe-Tyr-Met, Ser-Ser-Tyr-Tyr-Ser-Arg [SEQ ID NO:2], Phe-Pro-Lys-Phe-Phe-Ser-Arg-Gln [SEQ ID NO:3], Lys-Pro-Ile-Glu-Phe-Nph-Arg-Leu [SEQ ID NO:4], Gly-Pro-Leu-Gly-Ile-Ala-Gly-Gln [SEQ ID NO:5], Gly-Pro-Gln-Gly-Ile-Trp-Gly-Gln [SEQ ID NO:6], Gly-Phe-Leu-Gly [SEQ ID NO:7]. In addition, the enzymatically cleavable linker may contain a self-immolative linker such as a self-immolative p-aminobenzyloxycarbonyl (PABC) linker or a N-methyl- or symmetric N,N-dimethylethylene linker.

In another preferred embodiment of the composition of the present invention, the cleavable linker according to the present invention preferably contains at least one acid-labile bond. Examples of acid-labile bonds are ester, acetal, ketal, imine, hydrazone, carboxylhydrazone and sulfonylhydrazone bonds and bonds containing a trityl group.

In a further preferred embodiment of the composition of the present invention, the cleavable linker comprises a substituted or unsubstituted, branched-chain or straight-chain aliphatic alkyl group with 1 to 20 carbon atoms, which may comprise one or more oxygen or nitrogen atoms, and/or a substituted or unsubstituted aryl residue.

In a particularly preferred embodiment of the composition of the present invention, the cleavable linker is a carboxylic hydrazone linker.

According to the present invention, the term "in situ" includes the binding of the prodrug of the composition according to the present invention to an endogenous biomolecule, such as a serum protein, particularly serum albumin, inside the organism to which the prodrug has been administered.

The term "drug" as used herein relates to any compound which brings about a pharmacological effect either by itself or after its conversion in the organism in question, and thus also includes the derivatives from these conversions. The pharmacological effect of the drugs of the composition according to the present invention can be a single effect only, e.g. a cytostatic effect, or a broad pharmacological spectrum of actions, such as an immunosuppressive and antiphlogistic effect at the same time.

In a preferred embodiment of the composition of the present invention, the first drug and the second drug contained in the prodrug are independently selected from the group consisting of a cytostatic agent, a cytokine, an immunosuppressant, an antirheumatic, an antiphlogistic, an antibiotic, an analgesic, a virostatic, an antimycotic agent, a transcription factor inhibitor, a cell cycle modulator, a multiple drug resistance (MDR) modulator, a proteasome or protease inhibitor, an apoptosis modulator, a histone deacetylase inhibitor, an enzyme inhibitor, an angiogenesis inhibitor, a hormone or hormone derivative, a radioactive substance, a light emitting substance, or a light absorbing substance.

In a preferred embodiment of the composition of the present invention, the first drug and/or the second drug contained in the prodrug are each a cytostatic agent independently selected from the group consisting of N-nitrosoureas such as nimustine; the anthracyclines doxorubicin, daunorubicin, epirubicin, idarubicin, mitoxantrone, and ametantrone, and any derivatives thereof; the alkylating agents chlorambucil, bendamustine, melphalan, and oxazaphosphorines, and any derivatives thereof; the antimetabolites 5-fluorouracil, 2'-deoxy-5-fluoridine, cytarabine, cladribine, fludarabine, pentostatine, gemcitabine, and thioguanine, and any derivatives thereof; the folic acid antagonists methotrexate, raltitrexed, pemetrexed, and plevitrexed, and any derivatives thereof; the taxanes paclitaxel and docetaxel, and any derivatives thereof; the camptothecins topotecan, irinotecan, 9-aminocamptothecin, and camptothecin, and any derivatives thereof; the Vinca alkaloids vinblastine, vincristine, vindesine, and vinorelbine, and any derivatives thereof; calicheamicins and any derivatives thereof; maytansinoids and any derivatives thereof; auristatins and any derivatives thereof; epothilones and any derivatives thereof; bleomycin, dactinomycin, plicamycin, miromycin C and cis-configured platinum(II) complexes. In a particularly preferred embodiment of the composition of the present invention, the first drug and/or the second drug contained in the prodrug is/are doxorubicin, or a derivative thereof.

Especially suitable cytokines according to the present invention are, for example, interleukin-2, interferon α-2a, interferon α-2b, interferon β-1a, interferon β-1b, interferon γ-1b, tumor necrosis factor, and any derivatives thereof.

Especially suitable immunosuppressants according to the present invention are, for example, cyclosporin A, tacrolimus, sirolimus, everolimus, mycophenolatmofetil, and any derivatives thereof.

Especially suitable antirheumatics according to the present invention are, for example, methotrexate, leflunomid, sulfasalazine, chloroquine, and any derivatives thereof.

Especially suitable antiphlogistics and/or analgesics according to the present invention are, for example, salicylic acid derivatives such as for example acetylsalicylic acid, and any derivatives thereof; drug derivatives having an acetic or propionic acid group such as diclofenac or, respectively, naproxen, and aminophenol derivatives such as for example paracetamol.

Especially preferred antibiotics according to the present invention are, for example, sulfanilamide, sulfacarbamide and sulfamethoxydiazine, and any derivatives thereof; penicillins, for example 6-aminopenicillanic acid, penicillin G as well as penicillin V, and any derivatives thereof; isoxazolylpenicillins such as oxacillin, cloxacillin and clucloxacillin, and any derivatives thereof; α-substituted benzylpenicillins such as ampicillin, carbenicillin, pivampicillin, amoxicillin, and any derivatives thereof; acylaminopenicillins, for example mezlocillin, azlocillin, piperacillin, apalcillin, and any derivatives thereof; amidinopenicillins, for example mecillinam; atypical β-lactams such as imipenam and aztreonam; cephalosporins, for example cephalexin, cefradin, cefaclor, cefadroxil, cefixime, cefpodoxime, cefazolin, cefazedone, cefuroxime, cefamandole, cefotiam, cefoxitin, cefotetan, cefmetazole, latamoxef, cefotaxmine, ceftriaxone, ceftizoxime, cefmonoxime, ceftazidime, cefsulodin and cefoperazone, and any derivatives thereof; tetracyclines such as tetracycline, chlorotetracycline, oxytetracycline, demeclocycline, rolitetracycline, doxycycline, minocycline, and any derivatives thereof; chloramphenicols such as chloramphenicol and thiamphenicol, and any derivatives thereof; gyrase inhibitors, for example nalidixic acid, pipemidic acid, norfloxacin, ofloxacin, ciprofloxacin and enoxacin, and any derivatives thereof; and antituberculotics such as isoniazid, and any derivatives thereof.

Especially preferred virostatics according to the present invention are, for example, nucleoside analogs such as acyclovir, ganciclovir, idoxuridine, ribavirin, vidaribine, zidovudine, didanosine and 2',3'-dideoxycytidine (ddC), and any derivatives thereof, as well as amantadine.

Especially suitable antimycotic agents according to the present invention are, for example, amphotericin B, and any derivatives thereof.

Especially preferred MDR modulators according to the present invention are, for example, verapamil, dihydropyridins, cyclosporin A and D, tacrolismus, rapamyin, digoxin, digitoxin, quinidin, lovastatin, atorvastin, analogues of reserpine, trifluoperazine, pervilleines A-F, valspodar, dexverapamil, biricodar, bepridil, erythromycin, levofloxacin, losartan, morphin, rifampin, phenyloin, colchicin, rhodamin 123, amprenavir, indinavir, nelfinavir, saqunavir, ritonavir, XR9576, LY335979, OC-144093, R101933, GF120918, ONT-093, MS-209, S-9788, reversin 205 and 121, or any related derivative.

Especially preferred transcription factor inhibitors according to the present invention are, for example, compounds that inhibit activation of NF-κB such as alpha-lipoic acid, alpha-tocopherol, anetholdithiolthione (ADT), butylated hydroxyanisole (BHA), cepharanthine, caffeic acid phenethyl ester (3,4-dihydroxycinnamic acid, CAPE), catechol derivatives, diethyldithiocarbamate (DDC), diferoxamine, dihydrolipoic acid, disulfram, dimethyldithiocarbamates (DMDTC), curcumin (diferuloylmethane), EPC-K1 (phosphodiester compound of vitamin E and vitamin C), epigallocatechin-3-gallate (EGCG; green tea polyphenols), ethylene glycol tetraacetic acid (EGTA), glutathione, L-cysteine, lacidipine, melatonin, N-acetyl-L-cysteine (NAC), nordihydroguaiaritic acid (NDGA), phenanthrolines, pyrrolinedithiocarbamate (PDTC), quercetin, tepoxaline (5-(4-chlorophenyl)-N-hydroxy-(4-methoxyphenyl)-N-methyl-1H-pyrazole-3-propan-amide), vitamin C, vitamin E derivatives, alpha-torphryl succinate, alpha-torphryl acetate, PMC (2,2,5,7,8-pentamethyl-6-hydroxychromane), benzylsocyanate, resveratol, genistein, lupeol, lycopene, panepoxydone, epoxyquinomicin C, dehydroxymethylepoxyquinomicin (DHMEQ), cycloepoxydon, gliotoxin, as well as I-κB-alpha phosphorylation and/or degradation inhibitors such as PS-1, 145, aspirin, salicylic acid, BAY-11-7082 (E3[(4-methylphenyl)-sulfonyl]-2-propenenitrile), BAY-11-7085 (E3[(4-t-butylphenyl)-sulfonyl]-2-propenenitrile), cycloepoxydon; 1-hydroxy-2-hydroxymethyl-3-pent-1-enylbenzene, ibuprofen, prostaglandin A1, sanguinarine (pseudochelerythrine, 13-methyl-[1,3]-benzodioxolo-[5,6-c]-1,3-dioxolo-4,5 phenanthridinium), sulfasalazine, sulindac, capsaicin (8-methyl-N-vanillyl-6-nonenamide), emodin (3-methyl-1,6,8-trihydroxyanthraquinone), erbstatin (tyrosine kinase inhibitor), estrogen (E2), gliotoxin, genistein, resiniferatoxin, and miscellaneous inhibitors of NF-κB such as beta-amyloid protein, glucocorticoids (dexamethasone, prednisone, methylprednisolone), leptomycin B (LMB), o,o'-bismyristoyl thiamine disulfide (BMT), ADP ribosylation inhibitors e.g., nicotinamide, 3-aminobenzamide, bi-, tri, or tetracyclic lactames, 1,8-naphtalimide derivatives, phenanthridin-6-ones, 3,4-dihydro-5-methyl-isoquinolin-1 (2H)-one, benzoxazole-4-carboxamide, 1,6-naphthyridine-5 (6H)-ones, quinazolin[3,4-d]pyrimidin-4(3H)-ones, 1,5-dihydroxyisoquinoline, 2-methyl-quinazolin-4[3H]-ones, 1,11b-dihydro-[2H]benzopyrano[4,3,2-de]isoquinolin-3-one, atrial natriuretic peptide (ANP), atrovastatin (HMG-CoA reductase inhibitor), calcitriol (1a,25-dihydroxyvitamine D3), E3330 (quinone derivative), herbimycin A, hypericin, hydroquinone (HQ), KT-90 (morphine synthetic derivatives), mevinolin, 5'-methylthioadenosine (MTA), pentoxifylline (1-(5'-oxohexyl) 3,7-dimethylxanthine, PTX), phenyl-N-tert-butylnitrone (PBN), pituitary adenylate cyclase-activating polypeptide (PACAP), quinadril (ACE inhibitor), ribavirin, secretory leukocyte protease inhibitor (SLPI), serotonin derivative (N-(p-coumaroyl) serotonin), silymarin, vasoactive intestinal peptide (VIP), D609 (phosphatidylcholine-phospholipase C inhibitor), RO31-8220 (PKC inhibitor), SB203580 (p38 MAPK inhibitor), triptolide (PG490, extract of Chinese herb), LY294,002, mesalamine, wortmannin (fungal metabolite), or CHS 828 (N-(6-(p-chlorophenoxy)-hexyl)-N'-cyano-N''-4-pyridylguanidine), sesquiterpene lactones such as parthenoilde, helenalin, miller-9E-enolid and budlein A.

Especially preferred proteasome and protease inhibitors according to the present invention are, for example, peptide aldehydes: ALLnL (N-acetyl-leucinyl-leucinyl-norleucynal, MG101), LLM (N-acetyl-leucinyl-leucinyll-methional), Z-LLnV (carbobenzoxyl-leucinyl-leucinyl-norvalinal, MG115), Z-LLL (carbobenzoxyl-leucinyl-leucinyl-leucynal, MG132), Z-LLL-B(OH)$_2$ (MG-262), boronic acid derivatives, e.g. PS-273, PS-293, PS-296, PS-303, PS-305, PS-313, PS-321, PS-325, PS-334, PS-341, PS-364, PS-352, PS-383, lactacystine, beta-lactone, boronic acid peptide, ubiquitin ligase inhibitors deoxyspergualin, APNE (N-acetyl-DL-phenylalanine-beta-naphthylester), BTEE (N-benzoyl L-tyrosine-ethylester), DCIC (3,4-dichloroisocoumarin), DFP (diisopropyl-uorophosphate), TPCK (N-alpha-tosyl-L-phenylalanine chloromethyl ketone), TLCK (N-alpha-tosyl-L-lysine chloromethyl ketone), FK506 (Tacrolimus), Cyclosporin A.

Especially preferred apoptosis modulators according to the present invention are, for example, farnesyl transferase inhibitors, e.g. R115777, SCH66336, BMS214662, Imatinib, 17-AAG, EGFR inhibitors, e.g., ZD1839, MEK inhibitors, e.g., PD 032590, RAF inhibitors e.g., BAY43-9006, erlotinib, PKC inhibitors, e.g. UCN-01, PKC-412, Bryostatin, ISIS-3521, LY333531, safingol, CGP-41251 (midostaurin), lonidamine, apoptin, survivin, rapamycin, CCI-779, RAD001 (everolimus), PXD101, tyrosine kinase inhibitors, e.g. Iressa, OSI-774, STI-571, inhibitors of enzymes in the mitogen-activated protein kinase pathway e.g., PD-098059, U-0126.

Especially preferred histone deacetylase (HDAC) inhibitors are suberoyl-3-aminopyridineamide hydroxamic acid, M344, NVP-LAQ824, SB939, trichostatin A, vorinostat (SAHA), BML-210, cyclic tetrapeptides (such as trapoxin B), and the depsipeptides, benzamides such as entinostat (MS-275), CI994, mocetinostat (MGCD0103), electrophilic ketones and aliphatic acid compounds such as phenylbutyrate and valproic acid, AN-9, phenylbutyrate and valproic acid, belinostat (PXD101), apicidin, LAQ824, and panobinostat (LBH589); and Romidepsin (Istodax, FK228, FR901228), PCI-24781, Resminostat (4SC-201), Givinostat (ITF2357), AR-42, CUDC-101, sulforaphane, PCI-24781 and PCI-34051, Droxinostat, R306465 (JNJ-26481585), MC1568, and Pyroxamide (NSC 696085).

Especially preferred cell cycle modulators according to the present invention are, for example, flavopiridol, bryostain-1, roscovitine, BMS-387032, perifosine, or lovastatin.

Especially preferred enzyme inhibitors according to the present invention are, for example, inhibitors of γ-glutamyl cystine synthetase e.g., buthione, sulfoxime.

Especially preferred angiogenesis inhibitors according to the present invention are, for example, thalidomide, endostatin, celecoxib, ABT-510, combrestatin A4, dalteparin, dimethylxanthenone acetic acid, lenalidomide, LY317615 (enzastaurin), PPI-2458, ADH-1 (exherin), AG-013736, AMG-706, AZD2171, Bay 43-9006 (sorafenib), BMS-582664, CHIR-265, GW786034 (pazopanib), PI-88, PTK787/ZK 222584 (vatalanib), RAD001 (everolimus), SU11248 (sunitinib), suramin, XL184, ZD6474, ATN-161, or EMD 121974 (cilenigtide).

Especially preferred hormones or hormone derivatives according to the present invention are, for example, aminogluthemid, buserilin, cyproteronacetate, droloxifen, ethinylestradiol, flutamid, formesta, fosfestrol, gestonoroncaproate, goserilin, leuprolein, lynestrenol, medrogeston, medroxyprogesteronacetate, megestrolactetate, octreotid, tamoxifen, toremifin, triptorelin, anastrazole, exemestane, or letrozone.

For preparing the protein-binding prodrug of the composition of the present invention the second drug is bound to a linker through an acid-sensitive and/or hydrolytically and/or enzymatically cleavable bond. This derivatization is carried out with a suitable functional group of the second drug which is a HO—, NH$_2$—, HOOC—, HO$_3$S—, or carbonyl group. If the second drug does not contain a suitable functional group, then it is introduced through chemical modification, i.e. the above-mentioned drugs additionally include all derivatives that possess a HO—, NH$_2$—, HOOC—, HO$_3$S—, and/or carbonyl group.

In a particularly preferred embodiment of the composition of the present invention, the first drug and the second drug contained in the prodrug are the same. In a particularly preferred embodiment of the composition of the present invention, the first drug and the second drug contained in the prodrug both are doxorubicin. In an even more preferred embodiment of the composition of the present invention, the prodrug is DOXO-EMCH which is the 6-maleimidocaproyl (hydrazone) derivative of doxorubicin. In another preferred embodiment of the composition of the present invention, the first drug and the second drug contained in the prodrug are different.

A further aspect of the present invention relates to a combination of at least one first drug and at least one protein-binding prodrug, wherein the protein-binding prodrug comprises a protein-binding group, a second drug, and a linker that can be cleaved hydrolytically, enzymatically, or in a pH-dependent manner, for the simultaneous or sequential administration.

In the combination of the present invention, the at least one first drug and the second drug contained in the protein-binding prodrug may be the same or different from each other.

Herein, the term "combination" is not specifically restricted and e.g. relates to a combination of two or more compounds, or mixtures of compounds, which show a synergistic effect when used in a combined manner. A combination of the present invention may, for example, be represented by two different compounds or mixtures of compounds which are present in a separable or non-separable manner and show an improved effect when acting together. For example, a combination of the present invention may comprise two or more drugs which show improved pharmacological effects in combined use, when compared to the separate use of each of the individual drugs.

According to a specific embodiment, the combination of the present invention comprises two or more compounds or mixtures of compounds, which are present in separate containers, e.g. exerting a significant synergistic effect when used together.

Herein, the term "simultaneous administration" is not specifically restricted and means that the protein-binding prodrug and the at least one first drug are substantially administered at the same time, e.g. as a mixture.

Moreover, the term "sequential administration" used herein is not specifically restricted and means that the protein-binding prodrug and the at least one first drug are not administered at the same time, but instead that one of both is administered first and the other after a specific time interval.

In a further embodiment, the present invention relates to the above-defined combination, wherein in the sequential administration the protein-binding prodrug is administered before the at least one first drug or afterwards, and the time interval between the administration of the protein-binding prodrug and the at least one first drug is in the range of 2 minutes to 48 hours.

Generally, according to the present invention, the time interval between the administration of the protein-binding drug and the at least one first drug may be in the range of a few minutes to hours, such as in the range of 20 minutes to 36 hours, 30 minutes to 24 hours, or 1 to 12 hours. Further examples include time intervals in the range of 24 to 48 hours, 12 to 36 hours, 8 to 24 hours, and 6 to 12 hours. However, preferred intervals are 2, 5, 10, 15, 20, 30 and 45 minutes, and 1, 2, 3, 4, 6, 8, 10, 12, 16, 18, 20, 24, 28, 30, 32, 36, 40, 44 and 48 hours.

According to a further embodiment, in the combination of the present invention, the first drug and or the second drug, the protein-binding group and the cleavable linker are the same as defined above. In particular, if not mentioned otherwise, all definitions e.g. regarding the constituents or the properties of the above-defined composition also apply to the combination of the present invention.

The molar ratio of the first drug and the second drug contained in the protein-binding prodrug of the composition or the combination of the present invention is not particularly restricted. For example, the molar ratio of the first drug and the second drug is in the of 1:500 to 500:1, or of 1:100 to 100:1. According to a further example, the molar ratio is in a range of 1:50 to 50:1, or of 1:20 to 20:1. However, the molar ratio may also be in the range of 1:5 to 5:1, or may be 1:1.

The present invention further relates to a kit, comprising the composition or the combination as defined above, and optionally a pharmaceutically acceptable carrier and/or a pharmaceutically acceptable adjuvant and/or diluent. In the kit of the present invention, the protein-binding prodrug and the at least one first drug may be present as a mixture, e.g. in form of the above-defined composition, for simultaneous administration, or may be present in separate containers, e.g. in form of the above-defined combination, for subsequent administration.

In another aspect, the present invention relates to a pharmaceutical composition comprising the composition of the present invention, and optionally a pharmaceutically acceptable carrier and/or a pharmaceutically acceptable adjuvant and/or diluent.

The kit or the pharmaceutical composition of the present invention may for example contain solvents and diluents such as a sodium chloride solution or a solution containing any pharmaceutically acceptable buffers. Moreover, the pharmaceutical composition of the present invention may be in any form suitable for administration to a patient, for example in an injectable form, as a tablet or a capsule, or as a composition for inhalation.

According to a further embodiment the present invention, the kit or the pharmaceutical composition as defined above is for use in the treatment of a disease selected from the group consisting of cancer, autoimmune diseases, acute or chronic inflammatory diseases, or diseases caused by viruses and/or microorganisms.

In a further aspect, the present invention relates to the use of the composition of the present invention in the manufacture of a medicament for treating a patient suffering from a disease selected from the group consisting of cancer, autoimmune diseases, acute or chronic inflammatory diseases, or diseases caused by viruses and/or microorganisms.

A further aspect of the present invention relates to the composition, the combination, the kit, or the pharmaceutical composition as defined above for use in the treatment of a disease selected from the group consisting of cancer, autoimmune diseases, acute or chronic inflammatory diseases, or diseases caused by viruses and/or microorganisms.

In a further aspect, the present invention relates to a method for treating a patient suffering from a disorder or a disease such as cancer, autoimmune diseases, acute or chronic inflammatory diseases, or diseases caused by viruses and/or microorganisms, comprising the step of administering the composition, the combination, or the pharmaceutical composition as defined above.

The Figures show:

FIG. 1: Chemical structure of doxorubicin (A) and the prodrug DOXO-EMCH (B) which is a 6-maleimidocaproyl (hydrazone) derivative of doxorubicin.

Figure 2:
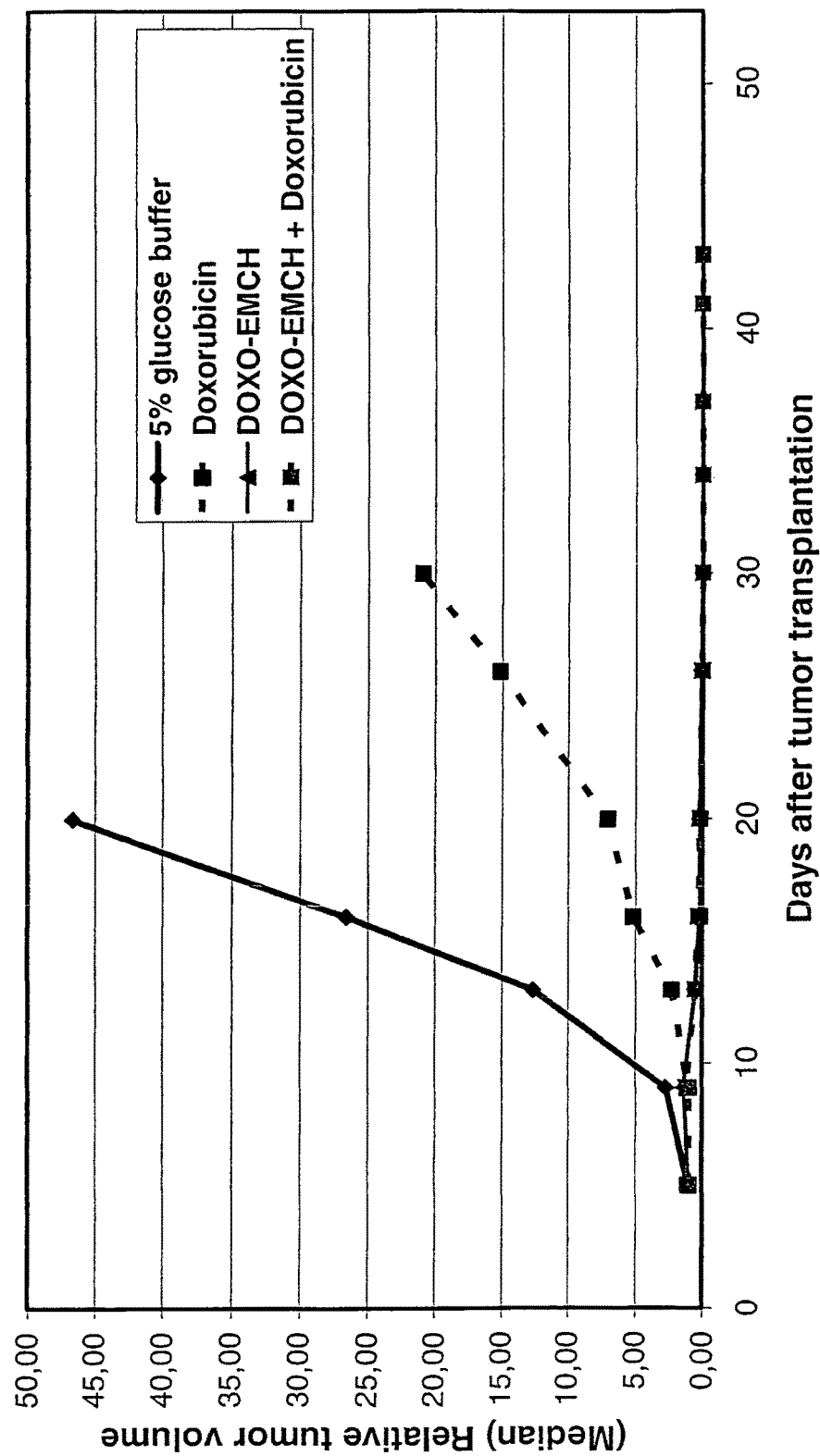

FIG. 2: Curves depicting tumor growth inhibition of subcutaneously growing A2780 xenografts under therapy with doxorubicin, DOXO-EMCH, and the combination of doxorubicin with DOXO-EMCH.

Figure 3:
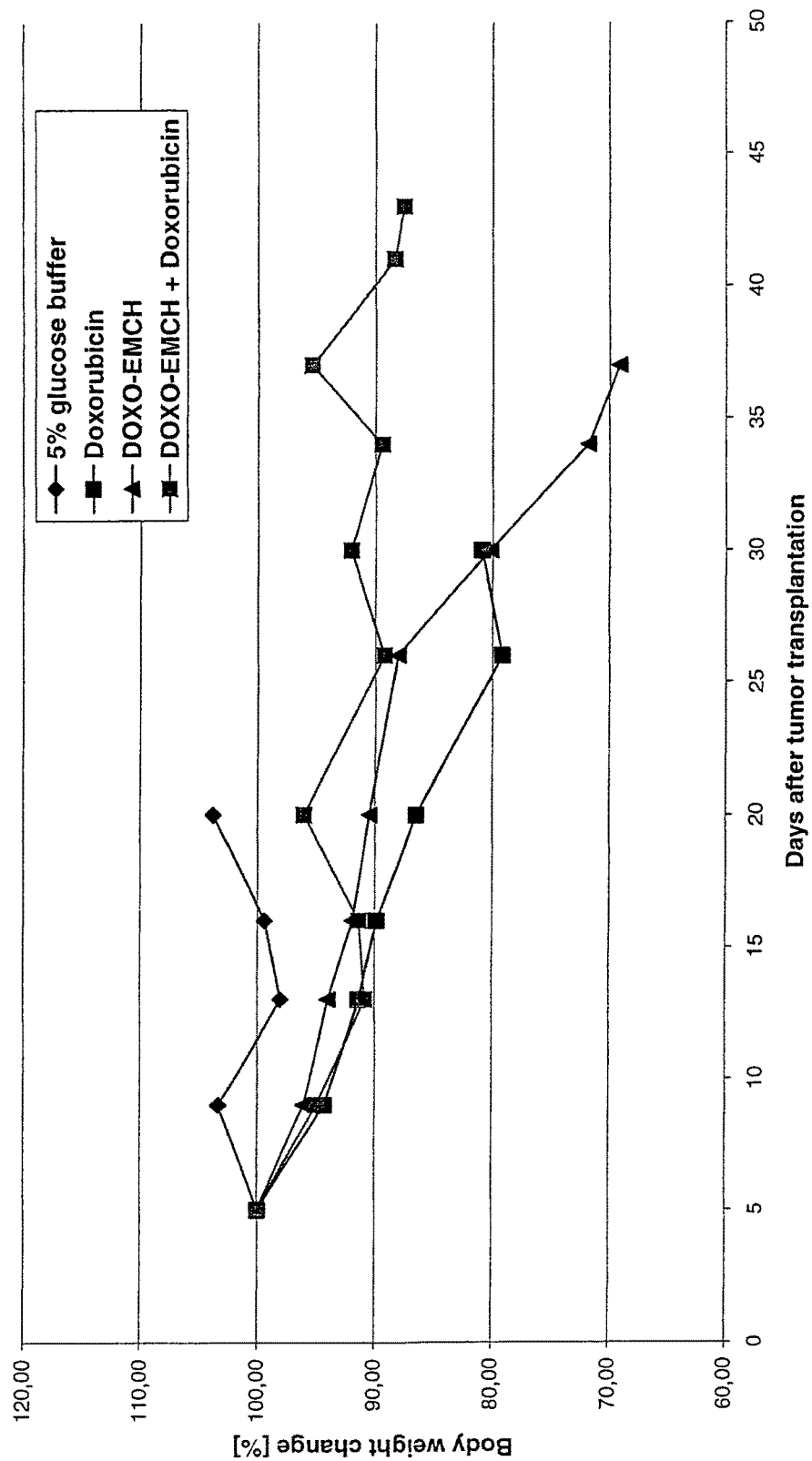

FIG. 3: Curves depicting body weight change (BWC in %) of mice with subcutaneously growing A2780 xenografts under therapy with doxorubicin, DOXO-EMCH, and the combination of doxorubicin with DOXO-EMCH.

The compositions of the present invention surprisingly and advantageously produce an improved efficacy and in vivo tolerability than either the first drug or the protein-binding prodrug alone. Accordingly, it is advantageously possible to efficiently treat a great variety of diseases by combining a protein-binding prodrug with a free drug of the same or a different type, whereby the advantageous properties of said drugs can be improved beyond the properties of the prodrug and the free drug alone.

The present invention will now be further illustrated in the following example without being limited thereto. Many further combinations according to the present invention can be realized as outlined above.

EXAMPLE

Example

Antitumor Efficacy of the Combination of Doxorubicin with the Prodrug DOXO-EMCH

The antitumor efficacy of the clinically established doxorubicin (FIG. 1 A), the 6-maleimidocaproyl(hydrazone)

derivative of doxorubicin (DOXO-EMCH; FIG. 1 B), and a combination of doxorubicin and DOXO-EMCH was assessed in the ovarian carcinoma A2780 xenograft model. DOXO-EMCH is an albumin-binding prodrug of doxorubicin that binds rapidly to the cysteine-34 position of circulating albumin and is taken up by solid tumors due to the enhanced permeation and retention effect (EPR effect). Following tumor uptake, DOXO-EMCH is cleaved in the acid environment of tumor tissue, either extra- or intracellularly.

DOXO-EMCH has a maximum tolerated dose (MTD) of 3×24 mg/kg body weight doxorubicin equivalents in nude mice and has shown superior efficacy over free doxorubicin in a number of xenograft and orthotopic tumor models. MTD of doxorubicin is 2×8 mg/kg body weight in nude mice models and higher doses, e.g. 2×12 mg/kg body weight, lead to unacceptable toxicity and mortality.

In order to evaluate the in vivo antitumor efficacy of a combination of doxorubicin with DOXO-EMCH in tumor-bearing mice, a direct comparison was made with a group treated with doxorubicin (2×8 mg/kg body weight) or DOXO-EMCH (3×24 mg/kg body weight doxorubicin equivalents) at their respective MTDs. For the combination, a lower dose of doxorubicin (3×4 mg/kg body weight) was combined with a lower dose of DOXO-EMCH (3×12 mg/kg body weight doxorubicin equivalents) wherein the DOXO-EMCH was administered 6 h prior to doxorubicin on the respective days of administration (cf. Table 1). The results of this experiment in the ovarian carcinoma A2780 xenograft model are shown in Table 1 and FIGS. 2 and 3.

With respect to antitumor efficacy, doxorubicin at its optimal dose of 2×8 mg/kg body weight only showed moderate antitumor efficacy up to day 30, after which the mice of this group had to be killed because of unacceptably high tumor burden. In contrast, treatment with DOXO-EMCH at 3×24 mg/kg body weight produced a pronounced antitumor effect which was statistically significant to the doxorubicin-treated group with tumor remissions for up to 37 days (cf. FIG. 2), after which some of the animals of this group died or were killed due to considerable body weight loss of over 30% (cf. FIG. 3). In contrast, the group treated with the combination of DOXO-EMCH (3×12 mg/kg body weight doxorubicin equivalents) and doxorubicin (3×4 mg/kg body weight) produced excellent antitumor effects which were statistically significant to the doxorubicin-treated group with stable tumor remissions for more than 40 days (cf. FIG. 3). Also, compared to the doxorubicin or DOXO-EMCH treated animals, significantly less body weight change (BWC) was observed (~12% at the end of the experiment) clearly indicating better tolerability (cf. FIG. 3). Thus, the treatment combining DOXO-EMCH with doxorubicin has a distinct advantage over treatment with doxorubicin or DOXO-EMCH alone with respect to antitumor efficacy and tolerability.

TABLE 1

Comparison of doses, mortality, relative tumor volumes, body weight change of doxorubicin, DOXO-EMCH, and the combination of DOXO-EMCH with doxorubicin against human ovarian cancer xenografts (A2780).

| Mice | Compounds | Schedule [days] | Dose (i.v.) [mg/kg/inject.] | toxic death | BWC [%] | RTV day 20 | RTV day 30 |
|---|---|---|---|---|---|---|---|
| 8 | Buffer | 6, 13, 20 | — | 0 | −2 | 50.3 | — |
| 8 | Doxorubicin | 6, 13 | 8 | 0 | −21 (d26) | 7.4 | 23.9 |
| 8 | DOXO-EMCH | 6, 13, 20 | 24 | 0 | −31 (d37) | 0.2 | 0.1* |
| 8 | Doxorubicin + DOXO-EMCH | 6, 13, 20 | 4 + 12 | 0 | −12 (d41) | 0.2 | 0.1* |

Ovar. Ca. A2780, 10E7 cells s.c., day 0,
NMRI: nu/nu mice, female
RTV: relative tumor volume,
BWC: body weight change
*significant to Doxorubicin Experimental procedure. In vivo efficacy studies were carried out with doxorubicin, the 6-maleimidocaproyl(hydrazone) derivative of doxorubicin (DOXO-EMCH), and a combination of doxorubicin with DOXO-EMCH in the ovarian carcinoma A2780 xenograft model. For in vivo testing, female NMRI: nu/nu mice (Taconic, Denmark) were used. The mice were held in individually ventilaged cages (IVC) under sterile and standardized environmental conditions (25±2° C. room temperature, 50±10% relative humidity, 12 hour light-dark-rhythm). They received autoclaved food and bedding (ssniff, Soest, Germany) and acidified (pH 4.0) drinking water ad libitum. A2780 tumor fragments were transplanted subcutaneously (s.c.) into the left flank region of anaesthetized mice (40 mg/kg i.p. Radenarkon, Asta Medica, Frankfurt, Germany) on day 0. Mice were randomly distributed to the experimental groups (8 mice per group). When the tumors were grown to a palpable size, treatment was initiated. Mice were treated intravenously (i.v.) with either glucose phosphate buffer (10 mM sodium phosphate, 5% D-(+)-glucose, pH 5.8), doxorubicin (2×8 mg/kg body weight), or DOXO-EMCH (3×24 mg/kg body weight doxorubicin equivalents), or a combination of DOXO-EMCH (3×12 mg/kg body weight doxorubicin equivalents) and doxorubicin (3×4 mg/kg body weight) with a 6 hour interval on the day of administration. DOXO-EMCH was dissolved in 10 mM sodium phosphate, 5% D-(+)-glucose, pH 5.8. The compounds were injected intravenously at weekly intervals on days 6 and 13 and on days 6, 13 and 20 for the remaining compounds. The injection volume was 0.2 ml/20 g body weight. Tumor size was measured twice weekly with a caliper-like instrument in two dimensions. Individual tumor volumes (V) were calculated by the formula V=(length×[width]2)/2 and related to the values on the first day of treatment (relative tumor volume, RTV). Statistical analysis was performed with the U-test (Mann and Whitney) with p<0.05. The body weight of mice was determined every 3 to 4 days.

The invention claimed is:

1. A method for enhancing efficacy and tolerability of a drug in a subject, said method comprising sequentially administering doxorubicin and a 6-maleimidocaproyl (hydrazone) derivative of doxorubicin (DOXO-EMCH) in a pharmaceutically acceptable carrier and/or a pharmaceutically acceptable adjuvant and/or diluent to the subject, wherein a time interval between the administrations of DOXO-EMCH and doxorubicin is 6 hours or less and wherein the molar ratio of DOXO-EMCH to doxorubicin ranges from 3:1 to 5:1.

2. The method according to claim 1, wherein the method is used for treatment of cancer.

3. The method according to claim 1, wherein the DOXO-EMCH is administered after the doxorubicin.

4. The method according to claim 1, wherein the DOXO-EMCH is administered before the doxorubicin.

5. A method for enhancing efficacy and tolerability of a drug in a subject, said method comprising simultaneously co-administering doxorubicin and a 6-maleimidocaproyl (hydrazone) derivative of doxorubicin (DOXO-EMCH) in a pharmaceutically acceptable carrier and/or a pharmaceutically acceptable adjuvant and/or diluent to the subject, wherein the molar ratio of DOXO-EMCH to doxorubicin ranges from 3:1 to 5:1.

* * * * *

SEQUENCE LISTING

<160> NUMBER OF SEQ ID NOS: 7

<210> SEQ ID NO 1
<211> LENGTH: 4
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 1

Ala Leu Ala Leu
1

<210> SEQ ID NO 2
<211> LENGTH: 6
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 2

Ser Ser Tyr Tyr Ser Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 3

Phe Pro Lys Phe Phe Ser Arg Gln
1               5

<210> SEQ ID NO 4
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug
<220> FEATURE:
<221> NAME/KEY: nph
<222> LOCATION: (6)..(6)
<223> OTHER INFORMATION: X = nitrophenylalnine

<400> SEQUENCE: 4

Lys Pro Ile Glu Phe Xaa Arg Leu
1               5

<210> SEQ ID NO 5
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 5

Gly Pro Leu Gly Ile Ala Gly Gln
1               5

```
<210> SEQ ID NO 6
<211> LENGTH: 8
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 6

Gly Pro Gln Gly Ile Trp Gly Gln
1               5

<210> SEQ ID NO 7
<211> LENGTH: 4
<212> TYPE: PRT
<213> ORGANISM: Artificial Sequence
<220> FEATURE:
<223> OTHER INFORMATION: Preferred peptide sequence incorporated in the
      prodrug

<400> SEQUENCE: 7

Gly Phe Leu Gly
1
```